United States Patent [19]

Bachalo

[11] 4,329,054

[45] May 11, 1982

[54] APPARATUS FOR SIZING PARTICLES, DROPLETS OR THE LIKE WITH LASER SCATTERING

[75] Inventor: William D. Bachalo, Dana Point, Calif.

[73] Assignee: Spectron Development Laboratories, Inc., Costa Mesa, Calif.

[21] Appl. No.: 67,116

[22] Filed: Aug. 16, 1979

[51] Int. Cl.³ ............................................. G01N 15/02
[52] U.S. Cl. ..................................... 356/336; 356/338
[58] Field of Search ............... 356/336, 338, 343, 345, 356/349, 351, 357

[56] References Cited

U.S. PATENT DOCUMENTS 4,211,487   7/1980   Morrison et al. .................... 356/336

OTHER PUBLICATIONS

Farmer, "Measurement of Particle Size, Number Density and Velocity Using a Laser Interferometer", *Applied Optics*, vol. 11, No. 11, pp. 2603-2612, Nov. 1972.

*Primary Examiner*—John K. Corbin
*Assistant Examiner*—Matthew W. Koren
*Attorney, Agent, or Firm*—Blakely, Sokoloff, Taylor & Zafman

[57] ABSTRACT

An apparatus for sizing particles, droplets or the like, particularly suited for determining the size of droplets in high number density sprays, is described. The apparatus employs the interferometer principle and off-axis collection to limit probe volume and to limit the light scatter detection to refraction and reflection. The central portion of the interference pattern is distinguished in an alternate embodiment by using a second laser beam as a pointer beam.

24 Claims, 7 Drawing Figures

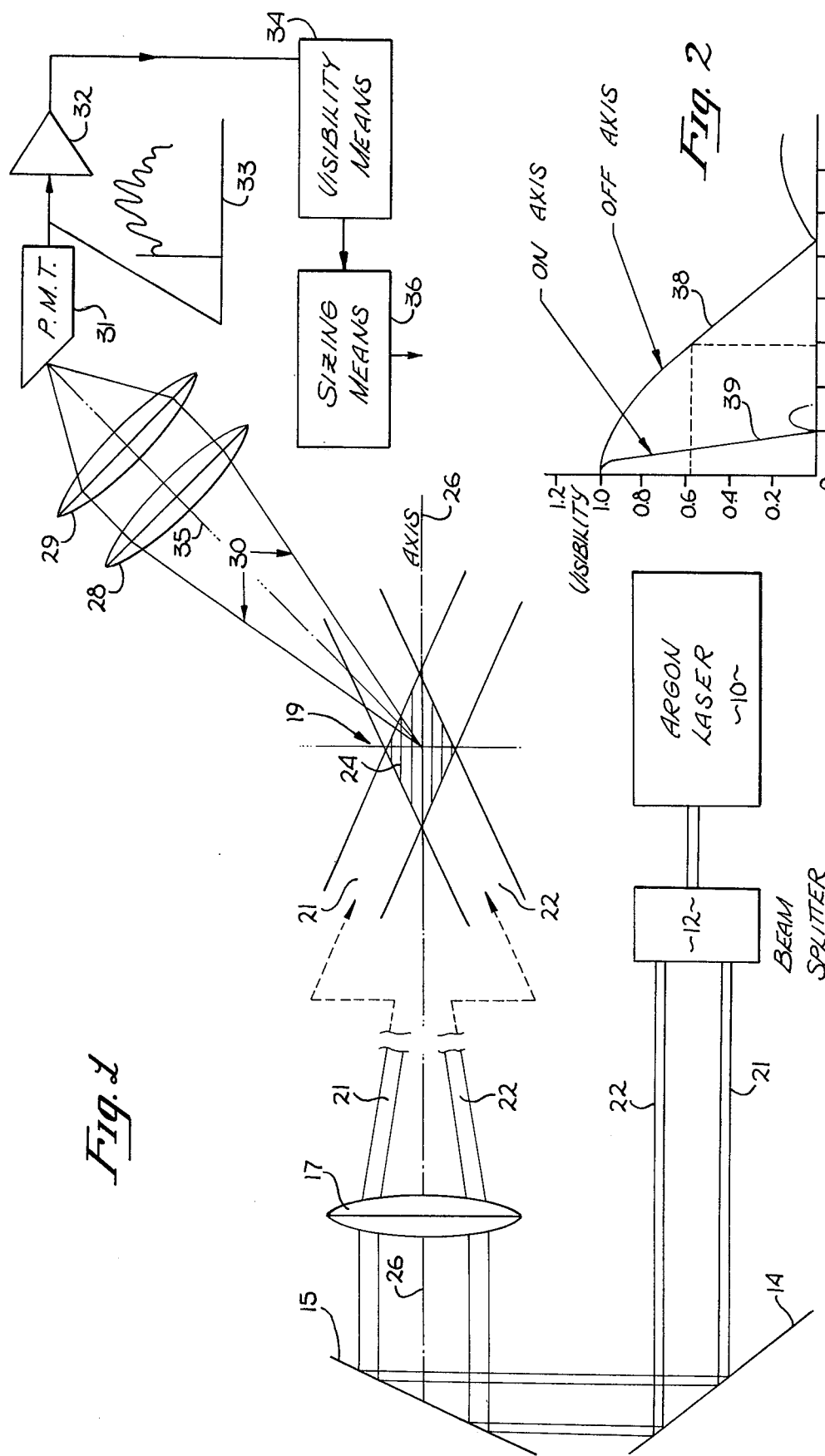

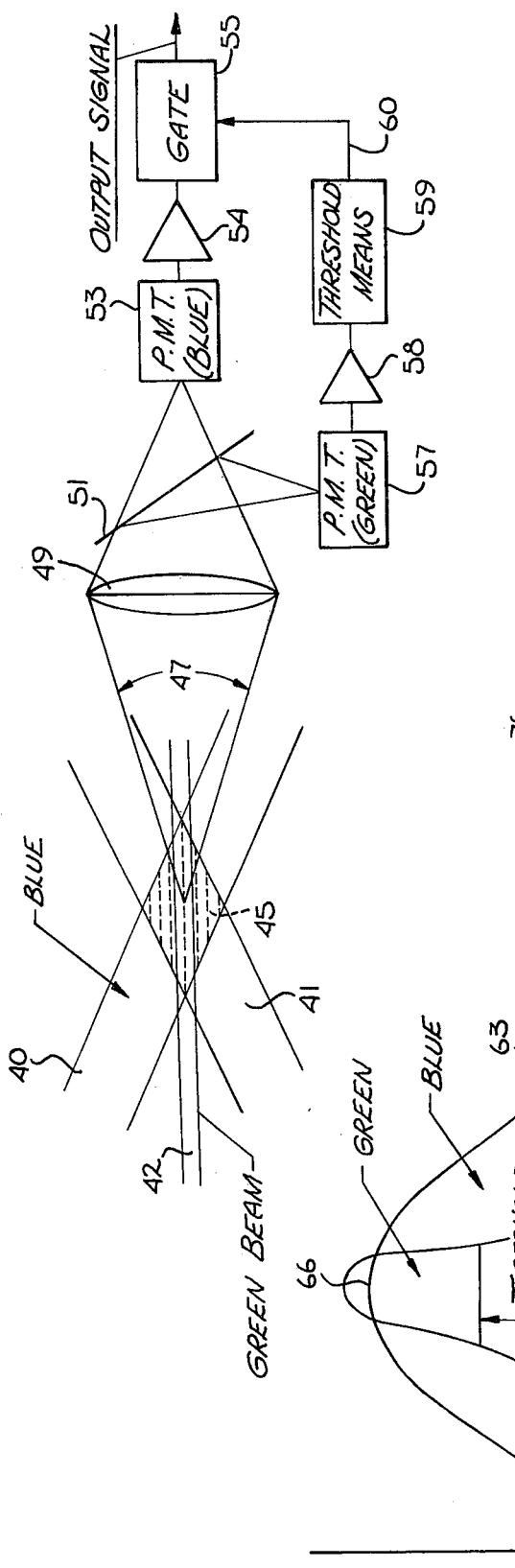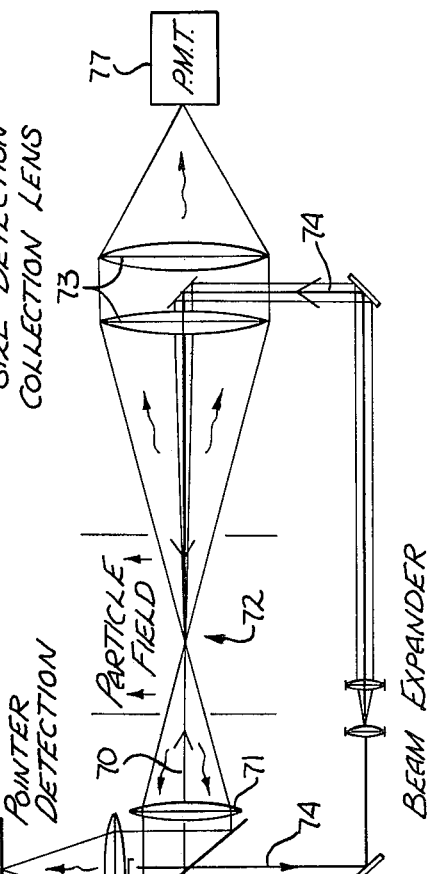

APPARATUS FOR SIZING PARTICLES, DROPLETS OR THE LIKE WITH LASER SCATTERING

BACKGROUND OF THE INVENTION

1. Field of the Invention

The invention relates to the field of determining parameters of particles, droplets or the like employing laser light scattering.

2. Prior Art

A number of techniques employing laser light scattering are well-known for determining both the size and velocity of particles. In one system, commonly referred to as a particle sizing interferometer, a pair of laser beams of equal intensity are caused to cross at the sample volume. An interference pattern between the beams is established by this crossing. Particles moving through this pattern scatter light in proportion to the spatially varying light intensity within the pattern. From this scattering, the information concerning both the particles' size and velocity can be computed. The particles' size is determined from the visibility. A more detailed explanation of this interferometer is given in "On-Line Particle Monitoring Instruments", by Bachalo, Geffken and Weth, 1978 *Symposium on Instrumentation and Control for Fossil Demonstration Plants,* June 19–21, 1978.

Significant for purposes of this patent is the fact that in these interferometers, the collection means used for determining particle sizing is always in-line or on-axis with the pair of laser beams which provide the interference pattern. It has been understood in the art that such on-axis collection for particle sizing was necessary. For example, see "The Interferometric Observations of Dynamic Particle Size, Velocity and Number Density", a dissertation presented to the Graduate Council of the University of Tennessee by W. Michael Farmer, March, 1973, at page 124.

There has long been a need to measure droplet size in sprays or the like. Such measurements are useful in aircraft icing studies, such as at engine inlets and other icing applications, weather studies (e.g., fog), fuel sprays in combustion applications, numerous nozzle sprays, etc. These measurements are also useful in determining the size of gas bubbles in liquids. The sizing techniques employed in the interferometer are difficult to use in these applications since the density of droplets is high when compared to typical particle densities found in flue gasses, etc. The sensed information from the interference pattern may represent scattering associated with multiple droplets. This information cannot readily be processed to determine particle size with this otherwise reliable system. The particle sizing interferometer is also limited in the size range (2 μm to 200 μm) over which it can be used.

The present invention discloses two techniques which permit particle sizing using the interferometric method. In the presently preferred embodiment, off-axis collection is employed to reduce the probe volume associated with the collection lens and to select the scattering phenonmena used to size the droplets. While off-axis collection has been employed for interferometer velocity determinations, as mentioned, it has been thought that such collection was not possible for sizing determinations. The problem with the prior art analysis, which led to the conclusion that the collection must be on-axis, is described.

In an alternate embodiment, the probe volume is "sharpened" by employing a second laser beam in addition to the pair of beams used to establish the interference pattern. As will be described, the second beam acts as a "pointer" to provide better fringe control. This results in more accurate parameter determinations. The use of the pointer beam also has application in light scattering instruments other than the interferometer, as will be discussed.

SUMMARY OF THE INVENTION

An apparatus for sizing particles, droplets or the like employing laser light scattering is disclosed as employed in the presently preferred embodiment. A laser generation means for generating a pair of coherent laser beams of the same wavelength and intensity is used. These beams are directed and focused by focusing means along a first axis and caused to cross at this first axis to establish an interference pattern. A collection means for sensing the scattering caused by the particles, droplets or the like in the interference pattern has a probe axis extending into the interference pattern. This probe axis is off-axis from the first axis. The visibility is determined from the information sensed by the collection means. A novel sizing means for establishing the size of a particle, droplet or the like from the visibility is coupled to the visibility determining means and provides an output signal representative of the size. The apparatus permits the sizing of a particle, droplet or the like and simultaneously measures the droplet velocity with an off-axis collection which substantially reduces the probe volume.

BRIEF DESCRIPTION OF THE DRAWINGS

FIG. 1 is a diagrammatical representation of the presently preferred embodiment of the invention.

FIG. 2 is a graph showing the relationship between visibility and size for both on-axis and off-axis collection.

FIG. 3 is a diagram illustrating the use of a pointer laser beam to distinguish the central portion of an interference pattern in an on-axis collection system.

FIG. 4 is a graph used to illustrate the manner in which the pointer beam reduces problems associated with the Gaussian intensity distribution within a laser beam.

FIG. 5a is an alternate embodiment of the pointer beam employing back scattering.

DETAILED DESCRIPTION OF THE INVENTION

Figure 5B:
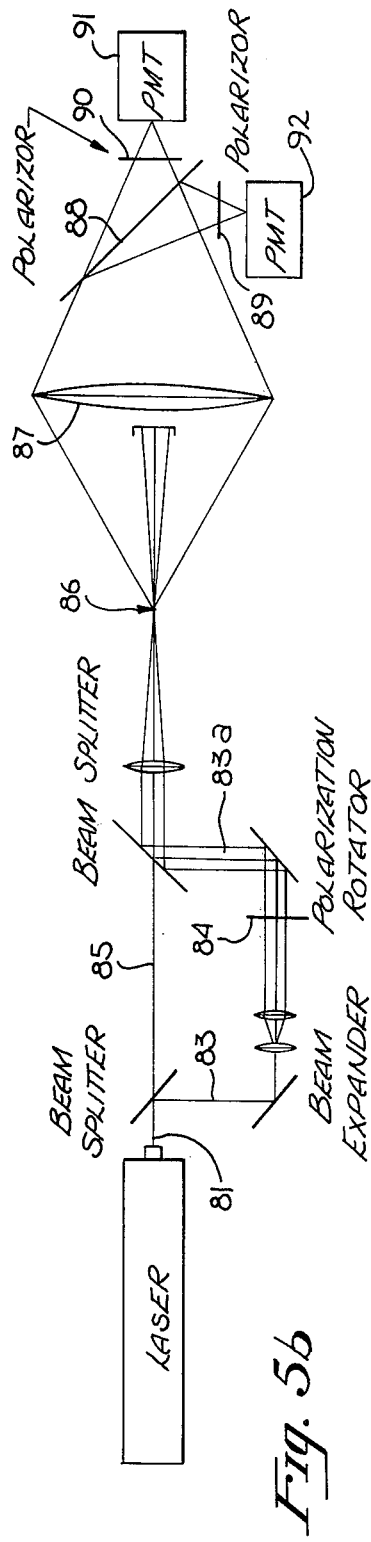
FIG. 5b is an alternate embodiment of the pointer beam employing polarization.

An apparatus for sizing particles, droplets or the like, particularly suited for determining the size of droplets in high number density sprays, is described. The apparatus employs the interferometer principle and off-axis collection to limit probe volume and to limit the light scatter detection to refraction and reflection. The central portion of the interference pattern is distinguished in an alternate embodiment by using a second laser beam as a pointer beam, as will be described. The use of the pointer beam has application in other laser devices employing scattering since it eliminates the uncertainty associated with the Gaussian distribution of the beam intensity. In the following description, numerous specific details are set forth, such as specific colors, etc.; however, it will be obvious to one skilled in the art that the invention may be practiced without these specific details. In other instances, well-known devices have been shown in block diagram form in order not to obscure the present invention in unnecessary detail.

Referring now to FIG. 1, the sizing apparatus includes a sample volume 19. The sample volume 19 is defined by the overlap region of the two focused laser beams from which light scattered by droplets or particles is admitted into the light detecting system. Particles, droplets, etc. moving with the flow under examination that pass through the sample volume are measured by the system of FIG. 1 and in particular by the collections means.

The laser beams employed in the interferometer device of FIG. 1 are generated, in the presently preferred embodiment, by an argon laser 10 (or helium-neon laser). The beam from this laser is split into two beams by the beam splitter 12. The beams 21 and 22 are, as is apparent, of the same wavelength and preferably of the same intensity. The beams are reflected from the reflectors 14 and 15 to the lens 17. The axis of the lens 17 is shown as axis 26. The lens 17 causes the beams 20 and 21 to cross through the axis within the sample volume 19. The crossing of these beams, as is well-known, establishes the interference (fringes) pattern 24. (Note that in FIG. 1, the beams 20 and 21 have been broken and then shown in enlarged form within the sample volume 19 in order to illustrate the interference pattern 24.)

The passage of the particles, droplets, etc. through the sample volume 19 causes scattered light in proportion to the spatially varying light intensity of the fringe pattern. As will be discussed, the scattered light through this pattern carries information concerning the particles' size and velocity. This scattering is sensed by a collection means which includes the lenses 28 and 29. These lenses define a probe volume 30 which extends into the sample volume and, more particularly, into the pattern 24. As is best shown in FIG. 1, the axis 35 associated with the probe volume is off-axis from the axis 26. In the presently preferred embodiment, these axes are separated by 10°, or greater.

By placing the axis 35 off-axis from the axis 26, the probe volume within the interference pattern is greatly reduced. Note that if the axis 35 were coincident with the axis 26, the collection means would receive light scattered by droplets passing over the extreme ends of the beam overlap region and even from the individual beams. Detection of that scattered light would introduce significant error into the size measurement.

The scattered light from the probe volume 30 is collected and focused through the lenses 28 and 29 onto a photomultiplying tube 31. The output of this tube after passing through a preamplifier 32 is coupled to the visibility means 34. Within the visibility means, the signal visibility is determined. The waveform from the photomultiplying tube 31 is shown on line 33 for a single particle. The visibility is proportional to the AC to DC ratio of this signal as is well-known in the prior art. Well-known circuits may be employed for determining the visibility. In the presently preferred embodiment, the signal representative of this visibility is converted to a digital signal by an analog-to-digital converter.

After the visibility has been determined, the digital signal representative of this visibility is coupled to a sizing means 36. This sizing means in the presently preferred embodiment comprises a memory and a microcomputer, which while not necessary is used for control functions and computations. The digital output from the visibility means is employed as an address for the memory and, in fact, the memory operates as a look-up table. The memory is programmed with the curve 38 shown in FIG. 2 (more precisely with the curves of FIG. 6). Thus, for each discrete visibility number, the corresponding size/fringe spacing data is placed within the memory. By way of example, if the visibility is approximately 0.58, the digital signal representative of this number is used to address the memory; the output of the memory is the number 4.5. The collection means, including the visibility means and sizing means of FIG. 1, are similar to prior art devices except for the program stored within the memory and the fact that the axis 35 of the probe volume is not coincident with the axis 26.

As previously mentioned, in the prior art a collection means for sizing was always used on-axis (that is, coincident with axis 26). The scattering was sensed and the visibility determined. Then in the manner described above, the sizing information was obtained from a look-up table. The look-up table was programmed with the curve 39 of FIG. 2. The analysis involved in arriving at curve 39 showed that off-axis collection was not possible for sizing. However, it has been determined through a re-examination of the mathematics associated with curve 39 that a new analysis could be developed to permit accurate sizing for off-axis collection. It is this off-axis collection which reduces the probe volume and allows the sizing of dense particles such as droplets in a spray and allows the sizing of droplets over a greater size range ($\sim 3$ $\mu$m to $\sim 5$ mm).

Geometrical optics laws, which are asymptotic approximations to laws for electromagnetic waves where applicable, greatly simplify the description of scattering from spheres. In general, the use of geometrical optics requires that $\alpha >> 1$ and the phase shift of a wave passing through the particle be large. That is, the index of refraction of the particle must differ sufficiently from the surroundings. Although there is no well-defined cutoff point on the applicability of these laws, comparisons to the exact Lorenz-Mie theory have been to show that the simplified theories offer remarkably good agreement down to a few microns.

It is known that for $\alpha > 10$, the scattering of electromagnetic radiation is separable into the simplified theories of diffraction, refraction and reflection (see *The Scattering of Light and Other Electromagnetic Radiation*, Academic Press, New York (1967) by H. Van de Hulst). Diffractive scatter is concentrated in a lobe in the forward direction which becomes smaller in width with increasing particle size. The other half of the incident radiation is scattered in all directions by reflection and refraction. In order to isolate the scatter due to diffraction from the reflective and refractive scatter components, off-axis light collection can be used. However, bounds must be established defining the minimum particle size and scattering angle for which diffractive scatter will be negligible relative to the scatter by refraction and reflection. The expressions for diffractive scattering intensity $$I_o(\theta,d) = \frac{\alpha^2}{4\pi}\left(\frac{\lambda J_1(\alpha \sin \theta)}{\alpha \sin \theta}\right) \tag{1}$$

where $\alpha = \pi d/\lambda$, $J_1$ is the Bessel function and for reflection (parallel polarization)

$$I_{1,1}(\theta) = \frac{1}{8\pi} \left( \frac{\sin(\theta/2) - [m^2 - 1 + \sin^2(\theta/2)]^{\frac{1}{2}}}{\sin(\theta/2) + [m^2 - 1 + \sin^2(\theta/2)]^{\frac{1}{2}}} \right) \quad (2)$$

and refraction $$I_{2,1}(\theta) = \quad (3)$$

$$\frac{2}{\pi} \left( \frac{m}{m^2 - 1} \right) \frac{(m\cos(\theta/2) - 1)^3 (m - \cos(\theta/2))^3 (1 + \sec^4(\theta/2))}{\cos(\theta/2)(m^2 + 1 - 2m\cos(\theta/2))^2}$$

can be used conveniently for this purpose. For example, it is known that for an index of refraction (m=1.5) and with particles as small as 2 μm, diffractive scatter is less than 10% of the total light scattered at 45°. The diffractive scatter decreases rapidly with angle for larger particles and for $\alpha > 15$, diffraction becomes insignificant at angles greater than 10°.

Although the present invention of using off-axis scatter detection may be usable for even smaller particles (0.5 to 2 μm) by describing the scatter with the exact Lorenz-Mie theory, the present description will be confined to particle sizes that can be treated with the simple geometric optics theory (>2 μm).

The analysis of the amplitude modulation of the laser Doppler velocimeter signal was developed by Farmer (see "The Interferometric Observation of Dynamic Particle Size, Velocity and Number Density", Ph.D. Thesis, University of Tennessee (1973)) to relate the signal visibility to particle size. Subsequently, a more vigorous approach was used to show the limitations of Farmer's work and demonstrated the additional parametric effects of the light collection aperture. Following the latter approach, it has been demonstrated that because the beamstops removed some of the scattered light fields they also had to be accounted for in the limits of integration over the aperture. Since the beamstops are indispensible when collecting on-axis forward scattered light and the scattered lobes became concentrated in the forward direction for large spheres, it became evident that this method was limited to particles that are less than about 200 μm in diameter. In addition, with paraxial light scatter detection, the relatively long depth of field produced a probe of such length as to create difficulties due to multiple particles inhabiting the probe volume at one time when attempting measurements in particle fields having high number densities. Sprays have typically high number densities and a large size range so the possibility of using off-axis scatter detection is attractive.

Following this more vigorous approach, the fields scattered from each of two crossed beams (such as from beams 21 and 22 of FIG. 1) are taken separately and designated $E_{s1}$ and $E_{s2}$. The total scattered field is $$E_s = E_{s1} + E_{s2} \quad (4)$$

and the intensity is $$I = \frac{1}{2n} E_{s1} E_{s2}^* \quad (5)$$

where E* is the complex conjugate and n is the wave impedance.

$$I = \frac{1}{n}\{|E_{s1}|^2 + |E_{s2}|^2 + 2|E_{s1}||E_{s2}|\cos\sigma\} \quad (6)$$

where $|E_s|$ is the magnitude of the complex quantity $E_s$ and $\sigma$ is the phase angle between the scattered fields, $E_{s1}$ and $E_{s2}$. The collected power at the collection lens is determined by integrating the scattered intensity over the collecting aperture:

$$ip \propto \int A \int |E_{s1}|^2 + |E_{s2}|^2 + 2|E_{s1}||E_{s2}|\cos\sigma \, dA \quad (7)$$

The output of the photodetector can be separated into two terms:

$$\int A \int |E_{s1}|^2 + |E_{s2}|^2 \, dA$$

which is defined as the pedestal d.c. component of the signal and $$2 \int A \int |E_{s1}||E_{s2}|\cos\sigma \, dA$$

which represents the Doppler or high frequency component. The magnitude of the ratio of these two components has been defined as the signal visibility:

$$V = 2 \left| \frac{\int A \int |E_{s1}||E_{s2}|\cos\sigma \, dA}{\int A \int \{|E_{s1}|^2 + |E_{s2}|^2\} \, dA} \right| \quad (8)$$

It remains to define the field amplitude functions for the scatter from large spheres. Using Van de Hulst's criteria, particles with large $\rho$ where $$\rho = 2\alpha(m-1) \quad (9)$$

the scattered light can be separated into terms representing that scattered by diffraction, reflection and refraction. The conditions of anomalous diffraction in the near forward direction and the phenomena of the glory and the rainbow must be avoided. Van de Hulst has set the lower limit as $\alpha = 10$ to 20 for the applicability of the refractive scattering formulate. Where these assumptions are valid, the scattered field amplitude functions can be written as $$S_1(\theta_i) = \alpha |\epsilon_1(\theta_i)| D(\theta_i)^{\frac{1}{2}} T_1(\theta_i) \quad (10)$$

where $$\epsilon_1(\theta_i) = \sin\tau_i - [m^2 - \cos^2\tau_i]^{\frac{1}{2}}, \quad (11)$$

$$D(\theta_i) = \frac{\sin\theta_i/2 \cos\theta_i/2}{2\sin\theta_i} \quad (12)$$

and $$\sigma_1(\theta_i) = \frac{3\pi}{2} + 2\alpha \sin\frac{\theta_i}{2} \quad (13)$$

If $\tau$ is the incident angle measured with respect to the surface tangent and $\theta$ the exist angle of a ray measured with respect to the bisector of the two transmitted beams, then substitution of the expression for the field amplitudes into equation (3) yields $$V = 2 \int A \int \{\alpha|\epsilon_1(m,\theta_1)|D(m,\theta_1)^{\frac{1}{2}}\}\{\alpha|\epsilon_1(m,\theta_2)|D(m,\theta_2)^{\frac{1}{2}}\} \cdot \quad (14)$$

-continued $$\frac{\cos[\sigma_1(m,\theta,\alpha) - \sigma_2(m,\theta_2,\alpha)] \, dA}{\int A \int \{\alpha|\epsilon_1(m,\theta_1)|D(m,\theta_1)^{\frac{1}{2}}\}^2 + \{\alpha|\epsilon_2(m,2) D(m_{12})^{\frac{1}{2}}\}^2 dA}$$

where the subscripts on $\theta$ and $\tau$ are for the two beams, note that can be brought outside of the integral and cancelled from the expression but the droplet size does remain in the phase factor. Thus, the variation in the signal visibility collected over a specific lens aperture is a measure of the relative phase shift between the light waves scattered from the two intersecting laser beams. Interference fringes formed by the relative shift in phase between the scattered rays have a spacing at the collecting lens that depends upon the angle of intersection between the two laser beams, the dimensionless size, $\alpha$, and the index of refraction, m, of the droplet material.

The scattered light must be integrated over the lens aperture since the location and size of the collection aperture determine the scattering angle, $\theta$. A simple numerical integration scheme can be used for this purpose. As in the case of forward scatter detection, the visibility is dependent upon the collection f/No. and shape of the collection aperture. The visibility for a particle of given size decreases with a decrease in f/No.

However, the general shape of the visibility curve is the same for different f/No. and off-axis collection angles. The off-axis collection angles are defined as the angle subtended at the measurement volume by the bisector of the two transmitted laser beam paths and the line to the center of the collection lens.

The computed visibility curves fall to zero at a much higher d/δ

$$\left(\text{where } \delta \text{ is the fringe spacing, } \delta = \frac{\lambda}{2 \sin \gamma/2}\right)$$

than for the on-axis case. This is due to the fundamental difference in the mechanisms producing the change in the signal visibility with particle size. In the case of diffractive scatter, the visibility is affected by the beam intersection angle and the width of the forward scattered lobes. Signal visibility, for that case, is a measure of the degree of overlap of the two lobes at the collection aperture and hence, is a field amplitude phenomenon.

A simplified manner of viewing the present phenomenon is to consider the droplet as a small spherical lens. At the intersection of the two laser beams, a standing wave pattern of interference fringes are formed and these fringes are magnified by the effective focal length of the small droplet. Different sized droplets produce proportionate magnifications. Whether the collection lens "sees" a single fringe at a time or part of the next as well determines the relative signal amplitude modulation or visibility.

It is remarkable that the visibility is the same function of d/δ throughout the entire size range from 3 μm to 5 mm since the phase dependence given by $$\sigma = \frac{3\pi}{2} + 2\alpha(\sin \tau - m \sin \tau')$$

shifts from a small $\alpha$ and larger angular path effective to a very large $\alpha$ and a very small angular path effect. Another significant observation is that the curve is the same for different f/No. and collection angles so that only the scale on the abscissae need to be changed with the various optical parameters. This simplifies the data handling requirements.

Figure 6:
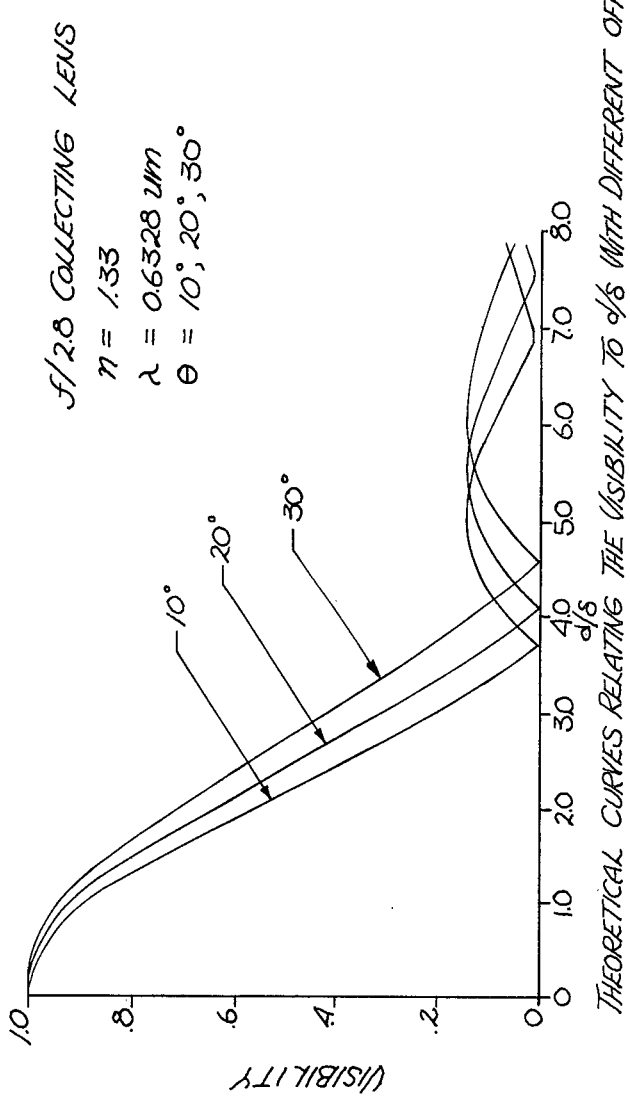
FIG. 6 illustrates curves, drawn to scale, showing the relationship between visibility and size for off-axis collection.

Thus, by plotting equation (14) as a function of dimensionless size (d/δ) using the relationships of equation (13) and $\alpha = \pi d/\lambda$ a curve such as curve 38 of FIG. 2 may be drawn. This permits the off-axis size determination not known in the prior art. In FIG. 6 actual curves drawn to scale form these equations for the stated apparatus are shown.

Referring now to FIG. 3, an alternate embodiment of the interferometer sizing apparatus of FIG. 1 is shown. In this embodiment, the central portion of the interference pattern is distinguished allowing better fringe control. A pair of laser beams 40 and 41 are again employed to establish the interference pattern. These beams pass through a lens system and are caused cross, establishing the interference pattern 45. The collection means includes the lens 49 having a probe volume 47.

For the embodiment illustrated in FIG. 3, the dual beams 40 and 41, which form the interference pattern, are blue light (e.g. wave length λ=0.488 μm). A beam of green light 42 is included on the bisector of the two blue beams, 40 and 41. For the illustrated embodiment, a beam expander is used to enlarge the green beam such that it will focus to a much smaller waist diameter than the crossed blue beams (e.g. 1/10). The blue beams in the interference region 45 are shown with the green beam 42 passing through the central portion of the interference pattern 45.

The reflector 51 passes the blue light, however reflects the green light. The scattered blue light is sensed by the photomultiplier tube 53 and amplified through the amplifier 54. Similarly, the scattered green light, which is reflected from the reflector 51, is sensed by the photomultiplier tube 57 and then amplified by the amplifier 58. (As is customary, the direct (non-scattered) green and blue light is not sensed by the tubes but rather strikes a non-active surface.)

The output of the amplifier 58 is passed through a threshold means 59. This means may be an ordinary thresholding device such as a Schmidt trigger, comparator, zener diode, etc. which passes a signal only when the input exceeds a predetermined level. When the scattered green light exceeds a predetermined level, a signal is coupled to the gate 55 on line 60 from the threshold means 59. Only when a signal is present on line 60 does gate 55 enable an output signal from the amplifier 54.

The output signal from the gate 55 is processed in a similar manner to the embodiment of FIG. 1; a visibility means and sizing means are employed for this processing. However, since the sensing is occuring on-axis, the curve 38 of FIG. 2 is applicable for sizing.

Assume that a particle passes through the interference pattern 45 of FIG. 3, but in a region which does not include the green light. The scattered blue light is sensed by the photomultiplier tube 53; however, the gate 55 is not activated. When a particle in the interference pattern passes through the green light, the scattering from this particle is sensed by the photomultiplier tube 57 and, if the scattering is sufficient, a signal is provided on line 60. At this time, the blue light, which is also scattered from the same particle, is allowed to pass through the gate 55 and to be processed. Thus, in order to receive an output signal for processing, a particle or the like must pass through the green beam and generally through the more central portion of this beam before the scattered blue light is sensed. As is apparent from FIG. 3, numerous particles within the interference pattern are ignored since they do not pass through the green beam. In this manner, better fringe control is achieved.

The use of the second green beam or "pointer" beam of FIG. 3 is of significant advantage where the magnitude of the scattering enters into the size, velocity, density, etc. determinations. Note that for the interferometer, the absolute magnitude of the scattered light is not significant. However, for many other instruments employing laser scattering, the magnitude of the scattering is of importance.

In a laser beam, as shown by curve 63 of FIG. 4, the light energy is distributed in a Gaussian fashion with lesser energy being present at the edges of the beam and greater energy in the central portion of the beam. When the scattered energy is sensed, the magnitude of the energy is dependent on where the particle crossed the beam. For example, a large particle passing through the edge of the beam may provide as much scattered energy as a small particle passing through the central portion of the beam. A number of solutions have been proposed to this problem, such as discussed in "Particle Size and Velocity Measurements by Laser Anemometry", AIAA 15th Aerospace Sciences Meeting, Los Angeles, California, January 24–26, 1977 by Yule, Chigier, Atakan and Ungut; and "An Optical Particle-Sizing Counter for In-Situ Measurements", Project Squid, Technical Report SU-2-PU, Purdue University, January, 1978 by Holve and Self.

The use of the second beam or pointer beam provides an easy solution to determining when a particle crosses the central portion of a beam. As shown in FIG. 4, the energy distribution of a second beam (green beam) is represented by the curve 64. This is the energy distribution where the pointer beam is focused within the central portion (flat intensity area) of the first beam (blue beam). If scattering from the blue beam is only sensed when scattering from the green beam exceeds the threshold 65, then the particle must be within the intensity level shown as the segment 66. This segment is relatively flat and provides scattering which is a true function of particle parameters rather than a function of where the particle crossed the beam.

The pointer beam, while shown in FIGS. 3 and 4 as employing different color laser beams, can be realized in a number of different ways and does not necessarily require two distinct wavelengths. For example, in FIG. 5a, a laser beam 69 is split into two beams. Beam 70 passes through the beamsplitter and transmitting lens 71 and is focused at the sample volume 72. Light scattered from the sample region formed by this beam 69 is collected in the forward direction by the collecting lens pair 73 and sensed by the collections means 77.

The beam 74 reflected from the beamsplitter is routed around the sample volume, expanded (to approximately 10 times the first beam diameter), and focused to a smaller diameter within the sample volume. Light scattered from this pointer beam is collected by the lenses 75 and focused to the detection means 76.

Each detection means receives the forward scatter from one beam and the backscatter from the other. However, the backscatter is typically two orders of magnitude less than the forward scatter and is, therefore significant. A threshold may be employed at the output of the photomultiplier tube 76 to enable signals from the photomultiplier tube 77. In this manner, when a signal is enabled from tube 77, the sensed light is from the central portion only of the main beam 70.

In FIG. 5b, another alternative for obtaining the pointer beam is shown. A polarized laser beam 81 is split and one beam 83 is expanded and passed through a rotational means 84 for rotating the polarity of this beam. The main beam 85 and the expanded beam 83a with the rotated polarity (by 90° with respect to the main beam) are recombined with a second beamsplitter. The beams are focused with the expanded pointer beam focusing to a much smaller diameter within the main beam at the sample volume 86. The scattered light is collected through the lens 87 and split by a beamsplitter 88. Polarizing filters 89 and 90 admit scattered light to each PMT of the respective polarization. Scattering from the main beam (PMT 91) is processed only if a simultaneous signal occurs on the PMT 92 detecting light from the pointer beam. Again thresholding of the signal from PMT 92 may be employed.

While the pointer beam and main beam described above are both laser light the above principle may be employed where one or both beams are non-coherent light such as from an incandescent lamp, or the like.

Thus, an apparatus for determining particle size employing the interferometer principle has been described. In one case, the probe volume is reduced by having off-axis collection and in another embodiment, the better fringe control is obtained by employing a pointer beam. The use of the pointer beam has wide application in other scattering measurements, since it eliminates the uncertainty caused by the projectory of a particle through the Gausseian energy distribution of a laser beam.

I claim:

1. An apparatus for sizing particles, droplets or the like, employing laser scattering comprising:
   laser generation means for generating a pair of laser beams of the same wavelength;
   focusing means situated to receive said pair of laser beams for directing and focusing said laser beams along a first axis and for causing said pair of laser beams to cross said first axis to establish an interference pattern between said pair of beams;
   collection means for sensing scattering of said pair of laser beams caused by said particles, droplets or the like in said interference pattern, said collection means having a probe axis extending into said interference pattern, said probe axis being off-axis from said first axis;
   visibility determining means for determining the visibility associated with said scattering, said visibility determining means coupled to said collection means; and
   sizing means for establishing the size of a particle, droplet or the like from said visibility, said sizing means coupled to said visibility determining means;
   whereby the size of a particle, droplet or the like is determined with an off-axis collection means.

2. The apparatus defined by claim 1 wherein said first axis is off-axis from said probe axis by at least 10°.

3. The apparatus defined by claim 2 wherein said laser generation means includes a laser and a beam splitter.

4. The apparatus defined by claim 3 wherein said collection means includes a lens and a photomultiplier tube.

5. The apparatus defined by claim 4 wherein said visibility determining means determines said visibility by ratioing the AC and DC components of the signal from said tube.

6. The apparatus defined by claim 5 wherein said sizing means includes a look-up table for providing sizing data as a direct function of said visibility.

7. The apparatus defined by claim 1 wherein a second laser beam is focused within said interference pattern, and wherein scattering from said second beam is sensed separately from said pair of beams, said separate sensing of said second beam being used to determine when sensing by said collection means of scattering from said pair of beams should be examined, whereby said second beam effectively reduces the probe volume of said collection means.

8. The apparatus as defined by claim 1 wherein the phase dependence of said beams is considered by said sensing means to determine the size of said particle, droplet or the like.

9. An apparatus for sizing particles, droplets or the like, employing laser scattering comprising:
    laser generation means for generating a pair of first laser beams of the same wavelength;
    focusing means situated to receive said pair of first laser beams for causing said pair of leaser beams to cross and thereby establish an interference pattern between said pair of beams;
    first collection means for sensing scattering of said pair of first laser beams caused by said particles, droplets or the like in said interference pattern, said collection means having a focal volume extending into said interference pattern;
    a second laser beam narrower than said first beams and distinguishable from said first beams, focused within said interference pattern;
    second collection means for sensing scattering of said second laser beam caused by said particles, droplets or the like in said focal volume of said first laser beam, said second collection means coupled to said first collection means for controlling output signals from said first collection means;
    whereby better fringe control within said interference pattern is achieved.

10. The apparatus defined by claim 9 wherein said first laser beams and said second laser beam are of different color.

11. The apparatus defined by claim 9 wherein said second collection means provides an output to enable said first collection means only when said scattering sensed by said second collection means exceeds a predetermined level.

12. In an apparatus for measuring or sensing parameters associated with particles, droplets, or the like, employing the scattering of a light beam, an improvement for determining when a particle, droplet, or the like has crossed the central portion of a first light beam comprising:
    light generation means for generating a second light beam, said second beam being disposed co-axially within said central portion of said first beam; and,
    sensing means for sensing the scattering of said second beam, said sensing means being substantially unaffected by the scattering of said first beam;
    whereby the passage of a particle, droplet, or the like through said central portion of said first beam which includes said second beam is detected by sensing the scattering of said second beam.

13. The improvement defined by claim 12 wherein said first and second beams are laser beams of different wavelengths.

14. The improvement defined by claim 13 wherein said first and second laser beams are generated by a single wavelength laser generation means.

15. The improvement defined by claim 12 wherein said first and second beams are of different polarization.

16. The improvement defined by claim 15 wherein said first and second beams are laser beams of the same wavelength.

17. The improvement defined by claim 12 wherein second beam is directed in an opposite direction to said first beam, said second beam being formed within said first beam.

18. The improvement defined by claim 17 wherein said first and second laser beams are of the same wavelength.

19. The improvement defined by claim 12 wherein said sensing means determines when said scattering exceeds a predetermined level.

20. A method for sizing a particle, droplet or the like, employing laser scattering which comprises:
    generating first and second laser beams of the same wavelength;
    focusing said first and second laser beams along a first axis and causing said first and second laser beams to cross said first axis to establish an interference pattern between said beams;
    sensing resulting scattered rays of said first and second laser beams caused by said particles, droplets or the like in said interference pattern, at an axis being off-axis from said first axis;
    determining the signal visibility associated with said scattering from the following relationship, $$V = 2 \left| \frac{\int A \int |E_{s1}| \, |E_{s2}| \cos \sigma \, dA}{\int A \int \{|E_{s1}|^2 + |E_{s2}|^2\} \, dA} \right|$$

where,
    V = signal visibility
    $E_{s1}$ = field scattered from said first beam
    $E_{s2}$ = field scattered from said second beam
    A = aperture area of collecting means
    $\sigma$ = phase angle between scattered fields $E_{s1}$ and $E_{s2}$, which is given by,
    $\sigma = 3\pi/2 + 2\alpha (\sin\tau - m\sin\tau')$
where,
    $\alpha = \pi d/\lambda$:
        $\lambda$ = wavelength of said pair of laser beams
        d = diameter of said particle, droplets or the like
    $\tau$ = incident angle of said first beam measured with respect to a surface tangent at the point of contact with said particle, droplet or the like
    $\tau'$ = angle of said first beam passing through said particle, droplet or the like with respect to said tangent
    m = index of refraction of said particle, droplet or the like
    determining the size of said particle, droplet or the like from said signal visibility;
    whereby the size of a particle, droplet or the like is determined by sensing scattered rays from a point off-axis from said first axis.

21. The method for sizing, as recited in claim 20, wherein said sensing is done off-axis by at least 10°.

22. The method for sizing, as recited in claim 21, wherein the generating step includes generating a single laser beam and splitting said beam using a beam splitter to form said first and second beams.

23. The method for sizing, as recited in claim 22, wherein said sensing step includes collecting said scattered rays by the use of a lens and detecting said collected rays by the use of a photo multiplier tube.

24. The method for sizing, as recited in claim 23, wherein said size is determined from said visibility by searching a look-up table which provides sizing data as a direct function of said visibility.

* * * * *